United States Patent [19]

Uyeo

[11] Patent Number: 4,629,726
[45] Date of Patent: Dec. 16, 1986

[54] PENEM CARBOXYLIC ACIDS

[75] Inventor: Shoichiro Uyeo, Kyoto, Japan

[73] Assignee: Shionogi & Co., Ltd., Osaka, Japan

[21] Appl. No.: 632,854

[22] Filed: Jul. 20, 1984

[30] Foreign Application Priority Data

Jul. 27, 1983 [JP] Japan ................... 58-138127

[51] Int. Cl.$^4$ .................. C07D 499/00; A61K 31/425
[52] U.S. Cl. ..................... 514/195; 514/196; 540/310
[58] Field of Search ........ 514/195, 196, 194; 260/245.2 R, 245.2 T

[56] References Cited

U.S. PATENT DOCUMENTS 4,464,299  8/1984  Uyeo ..................... 260/245.2 R
4,485,110 11/1984  Osborne ................ 260/245.2 T Primary Examiner—Nicholas S. Rizzo
Attorney, Agent, or Firm—Wenderoth, Lind & Ponack

[57] ABSTRACT

A 2-substituted or unsubstituted-6-(2-oxo-1, 3-dioxolan-4-yl)-2-penem-3-carboxylic acid derivative represented by the following formula (Ia) and:

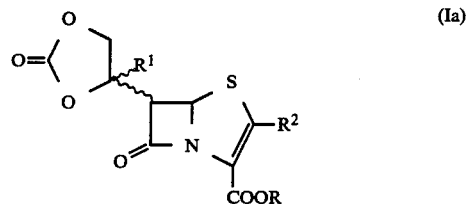

wherein R is hydrogen, a light metal or a carboxy-protecting group, $R^1$ is an alkyl group, $R^2$ is hydrogen, methyl or a substituted methyl group. The compounds have antibacterial activity.

5 Claims, No Drawings

PENEM CARBOXYLIC ACIDS

The present invention relates to 2-substituted or unsubstituted-6-(2-oxo-1,3-dioxolan-4-yl)-2-penem-3-carboxylic acid derivatives represented by the formula (Ia) and, their therapeutical use, processes for preparing them and pharmaceutical compositions containing them:

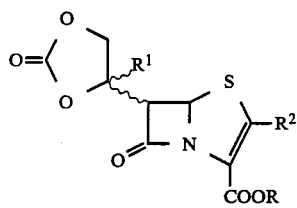

(Ia)

wherein R is hydrogen, a light metal or a carboxy-protecting group; $R^1$ is an alkyl group; $R^2$ is hydrogen, methyl or a substituted methyl group.

In the above definitions, the term "light metal" denotes a metal belonging to the second to forth period of the groups I to III in the periodic table, which provides a physiologically acceptable ion in the body fluid. Lithium, sodium, potassium, magnesium, aluminium and calcium are representative of the light metal.

The term "carboxy-protecting group" refers to any of the protecting groups which are commonly employed in the penicillin-cephalosporin art for the protection of the carboxylic group at the 3- or 4-position of a penicillin or cephalosporin compound and which can be readily removed without adversely affecting the remaining part of the molecule. Illustrative of these protecting groups are an aralkyl radical (e.g. benzyl, methylbenzyl, dimethylbenzyl, methoxybenzyl, ethoxybenzyl, nitrobezyl, aminobenzyl, diphenylmethyl, phthalidyl, phenacyl, etc.), a substituted alkyl radical (e.g. trichloroethyl, tert.-butyl, allyl, etc.), and an aryl radical (e.g. pentachlorophenyl, indanyl, etc.). This term further includes an ester residue formed by the reaction between the carboxylic acid at the 3-position and a N-hydroxyamino compound such as acetone oxime, acetophenone oxime, acetoaldoxime, N-hydroxysuccinimide or N-hydroxyphthalimide, an acid anhydride residue formed by the reaction between the carboxylic acid and carbonic acid or any other carboxylic acid, and a highly reactive amide residue formed by the reaction between the carboxylic acid and an amine such as a substituted amine or a substituted hydrazine.

The carboxy-protecting groups mentioned above may carry as a substituent an alkyl, cyanoalkyl, carboxyalkyl, carbamoylalkyl, hydroxamoylalkyl, alkoxamoylalkyl, aminoalkyl, N-alkylated aminoalkyl, ureidoalkyl, haloalkyl, carbamoylhaloalkyl, arylthioalkyl, heterocyclethioalkyl, sulfamoylalkyl, alkenyl, carboxy, amino, nitro, hydroxy, or oxo group or a halogen atom. These substituents may be additionally substituted by any one of the groups and atom just mentioned above. Furthermore, the carboxy, carbamoyl, amino, hydroxy or oxo moiety contained in the substituents may be modified with a conventional protecting group. In addition, two or more of these substituents may combine together to form a ring.

These substituents mentioned above will be referred to as "common substituents" hereinafter.

Especially preferred carboxy-protecting groups are an alkyl ester-forming group such as alkyl, alkanoyloxyalkyl, alkoxyalkyl or aminoalkoxyalkyl, an aralkyl ester-forming group such as benzyl, p-nitrobenzyl, phenacyl or phthalidyl, and an aryl ester-forming group such as phenyl or halophenyl.

The term "alkyl group" employed in connection with the symbol $R^1$ refers to any of lower alkyl groups such as methyl or ethyl.

Finally, the term "substituted methyl" in the definition of $R^2$ includes halomethyl, acyloxymethyl, heterocyclic thiomethyl and dimethyl-tert.-butylsilyloxy groups.

Chloromethyl is a preferred example of the halomethyl.

Preferable examples of an acyloxymethyl group are an alkanoyloxymethyl group such as acetyloxymethyl, an acyloxymethyl group derived from carbonic acid, a carbamoyloxymethyl group, and those in a protected form. However, aralkanoyloxymethyl, aroyloxymethyl, alkylsulfonyloxymethyl and arylsulfonyloxy methyl groups are also exemplified as the acyloxymethyl group.

The heterocyclic moiety in the heterocyclic thiomethyl group is a 5 or 6 membered, mono or bicyclic, conjugated heterocyclic group having at least one hetero atom selected from the group consisting of nitrogen, oxgen and sulfur atoms. The heterocyclic group may be optionally substituted with one or more of the aforementioned common substituents.

Five membered heterocyclic groups having 3 or 4 hetero atoms are most preferred. Specific examples of the most preferred heterocyclic groups are triazole, oxadiazole, thiadiazole, tetrazole as well as imidazole, triazine and dihydrotriazine.

The compounds of the formula (Ia) exhibit a strong antibiotic activity to various microorganisms and, also to those resistant to different antibiotics.

Thus, the compounds (Ia) are valuable antibiotics against various Gram positive and negative bacteria, and useful as drugs for human and veterinary uses. They can be used for treating or preventing infections caused by Gram positive bacteria (e.g. *Staphylococcus aureus, Streptococcus pyogenes, Bacillus subtilis, Bacillus cereus, Diplococcus pneumoniae, Corynebacterium diphtheriae*) and Gram negative bacteria (e.g. *Escherichia coli, Klebsiella pneumoniae, Proteus mirabilis, Proteus vulgaris, Proteus rettgeri, Proteus morganii, Enterobacter cloacae, Shigella sonnei, Salmonella paratyphi, Salmonella typhi, Serratia marsescens*), including anaerobic bacteria (e.g. *Bacteroides fragilis, Clostridium perfringens*). The compounds can be used also as disinfectants for preventing decay of perishables, additives to foodstuffs, or preventing bacterial growth of hygenical materials.

The compounds (Ia) can be used in a wide variety of oral or parenteral dosage forms solely or in admixture with other coacting substances. The pharmaceutical compositions may be a mixture of 0.01 to 99% of compound (Ia) with a pharmaceutical carrier which can be a solid material or liquid material in which the compounds are dissolved, dispersed, or suspended. They can be in a unit dosage form. The solid compositions can take the forms of tablets, powder, dry syrup, troches, granules, capsules, pills, suppositories, or like solid preparations. The liquid compositions can take the forms of injections, ointments, dispersions, inhalant, suspensions, solutions, emulsions, syrups, or elixirs.

They may be flavored and colored, and tablets, granules and capsules may be coated.

All of diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium alginate, tragacanth, carboxymethylcellulose, syrup, sorbitol, polyvinylpyrrolidone); disintegrators (e.g. starch, agar, carbonates, sodium laurylsulfate); lubricant (e.g. stearic acid, talc, paraffin, boric acid, silica, sodium benzoate, polyethylene glycol, cacao oil, magnesium stearate); emulsifying agents (e.g. lecithin, sorbitan monooleate, glycerin dioctanoate, acacia); suspending agents (e.g. sorbitol, methyl cellulose, glucose, sugar syrup, gelatin, hydroxyethylcellulose, carboxymethylcellulose, aluminum stearate gel, hydrogenated fats); solvents (e.g. water, buffer, peanut oil, sesame oil, methyl oleate); preservatives (e.g. methyl or ethyl p-hydroxybenzoate, sorbic acid); edible coloring agents, aromatic substances, solubilizing agents, buffers, stabilizing agents, analgesics, dispersing agents, wetting agents, antioxidants, and the like can be used, if the agents do not exert adverse effect on the compounds, according to the methods conventional in the art.

The compounds (Ia) wherein R is a light metal are soluble in water and conveniently used as a solution for oral administration or intravenus, intramuscular or subcutaneous injection according to a conventional method. The compounds can be dissolved in aqueous or oily solvents for injection to give a solution in an ampoule, but generally, more prolonged storage are possible by making a vial preparation containing crystals, powder, microcrystals or lyophilizate of compound (Ia), and dissolving or suspending the drug before use with the said solvents for injection. The vial preparation or injection can be given to a patient at a daily dose of e.g. 0.2 to 5 g depending on the infected bacteria, condition of the patient, and interval of the administration.

The compounds (Ia) in the form of a pharmaceutically acceptable esters (e.g. indanyl, acetoxymethyl, pivaloyloxymethyl, ethoxycarbonyloxyethyl, phenacyl, phthalidyl, phenyl, tolyl, xylyl, methoxyphenyl esters) can be absorbed through the digestive organ to some extent, and can be administered to human or veterinary subjects as powder, tablets, granules, capsules, dry syrup, emulsions, solution, suspension, and like oral preparations. They may be pure compounds or a composition comprising the compound (Ia) and pharmaceutical carriers. The preparation can be made according to the methods conventional in the art, and can be administered to a patient at a daily dose of e.g. 1 to 2 g depending on the condition of patient and the disease involved.

This invention also provides a method for treating or preventing human or veterinary bacterial infections by administering to the human or animal subject an effective amount of compound (Ia) at a daily dose of e.g. 0.2 to 5 g for injection or e.g. 1 to 2 g for oral administration, or 10 µg to 1 g for topical application, at an interval of e.g. 3 to 12 hours.

The method is applicable for treating or preventing some diseases caused by bacteria sensitive to compounds (Ia), e.g. pneumonia, bronchitis, pneumonitis, empyema, nasopharyngitis, tonsillitis, rhinitis, dermatitis, pustulosis, ulceration, abses, wound and soft tissue infections, ear infections, osteomyelitis, septicemia, gastroenteritis, enteritis, respiratory or urinary tract infections, and pyelonephritis when caused by bacteria sensitive to compound (Ia).

Preferably the compounds (Ia) are given to a patient in forms of pharmaceutical preparations e.g. powder, dry syrup, tablets, troches, granules, capsules, pills, suppositories, injections, ointments, dispersions, inhalant, suspensions, solutions, emulsions, syrups, and elixirs. They may be in a unit dosage form e.g. tablets, troches, capsules, injections, vials, granules or powder in a separate container or package.

All of the pharmaceutical preparations listed above can be prepared in a conventional manner.

It will be readily understood to those in the art that the compounds (Ia) can also be used as germicides or anticeptics. In addition, they are useful as a starting material for preparing some other compounds of the formula (Ia) and as an antibiotic agent for testing the sensitivity of microorganisms.

Preferred compounds (Ia) of the invention are those wherein R is sodium, potassium, diphenylmethyl, p-methoxybenzyl, phthalidyl, 2-oxo-dioxolenylmethyl, acetoxymethyl, 1-(ethoxycarbonyloxy)ethyl or pivaloyloxymethyl.

The compounds of the formulae (Ia) can be prepared by various methods detailed below:

1. Preparation of salts

The reaction of the compound (Ia) wherein R is hydrogen with a base or a salt of a weaker carboxylic acid results in the compound (Ia) wherein R is a light metal. The reaction may be carried out according to a conventional method known to the art. Preferred methods are the neutralization of the free acid (Ia) with a light metal bicarbonate. Alternative method is the exchange reaction of the free acid (Ia) with a salt of a lower carboxylic acid in a polar organic solvent such as alcohol, ketone or ester, followed by the addition of a solvent to which the desired salt (Ia) is sparingly soluble.

The above reactions complete after one to ten minutes when carried out at a temperature below 50° C. If necessary, the reaction mixture can be kept for a longer time unless any side reaction occurs.

2. Elimination of carboxy-protecting group

The compound of the formula (Ia) wherein R is a carboxy-protecting group can be converted to the compound (Ia) wherein R is hydrogen according to any of the conventional deprotecting reactions described below.

In the following description, the carboxy-protecting group will be sometimes represented by the name corresponding to the group formed by the reaction between the carboxylic acid and the compound employed for protecting the carboxylic acid, only for the purpose of avoiding the complexity of description. Thus, the protecting group "R" contained in the moiety of the formula:

—COOR will be referred to as "ester" for convenience.

(a) The compounds (Ia) having highly reactive protecting groups can be deprotected by contact with an acid, a base, a buffer or an ion exchange resin in an aqueous solution. Less reactive protecting group such as trichloroethyl, p-nitrobenzyl or phenacyl ester can be eliminated by treating it with a combination of a metal and an acid or with a dithionate, or by a catalytic reduction.

(b) Aralkyl esters may be eliminated by a hydrogenation using, e.g., palladium or nickel as a catalyst.

(c) Aralkyl esters, cyclopropylmethyl esters and sulfonylethyl esters can be eliminated through solvolysis using a mineral acid, a Lewis acid, a sulfonic acid, or a strong carboxylic acid and, if necessary, in the presence of a cation scavenger.

(d) Phenacyl esters, alkenyl esters and hydroxyaralkyl esters can be removed by the action of a base or a nucleophile. A photochemically active phenacyl ester can be eliminated by light irradiation.

(e) A 2-alkynyl ester can be converted to an alkali metal salt by reaction with an alkali metal alkanoate and palladium triphenylphosphine.

(f) The other conventional processes known for deprotecting carboxy-protecting groups can be employed in the present invention.

3. Introduction of a heterocyclic-thio group

The compounds (Ia) wherein $R^2$ is a heterocyclic thiomethyl can be obtained by the reaction between the compound (Ia) wherein $R^2$ is methyl substituted by a leaving group and a corresponding heterocyclic thiol or its reactive derivative. Preferred leaving groups are halogen, sulfonyloxy and alkanoyloxy. Preferred reactive derivatives of the heterocyclic thiol are an alkali metal salt and an ammonium salt of the thiol. The reaction can be conducted at temperature between 0° C. and 60° C. in an anhydrous solvent or an aqueous solvent. The reaction may be optionally accelerated by the addition of a dehydrating agent or phosphoryl chloride.

4. Cyclization

As illustrated in Example 2, the compound (Ia) of the invention can be obtained by heating under reflux a suitable carbonyl-alkylidenephosphorane compound in an appropriate solvent, whereby the compound undergoes ring closure to form a penem ring. The preferable solvents employed in this reaction are benzene, toluene and xylenes.

5. Preparation of pharmaceutically active ester

The compound of the formula (Ia) wherein R is a carboxy-protecting group can be converted, after elimination of the protecting group according to the aforementioned procedure, to the compound (Ia) having a pharmaceutically active ester group. For instance, the compound (Ia) wherein R is pivaloyloxymethyl can be obtained by reacting the compound (Ia) wherein R is hydrogen with pivaloyloxymethyl iodide in dimethylformamide (DMF) at temperature between 0° C. and room temperature in the presence of a base such as triethylamine.

6. Protection of carboxylic acid and other reactive functional groups

In carrying out the foregoing various reactions, it may be sometimes necessary to protect reactive functional groups other than the reacting group involved in the intended reaction. For this purpose, a variety of conventional techniques for the protection are all applicable to the processes of the invention. Such techniques are, for example, disclosed in the literatures, such as J. F. W. McOmie Ed., "Protective Groups in Organic Chemistry", pp183, PLEUM Press, N.Y., 1973; S. Patai, Ed., "The Chemistry of Functional Groups", pp505, Interscience Publ., John Wiley & Sons Ltd. London, 1969; and Flynn Ed., "Cephalosporins and Penicillins", Academic Press, N.Y. 1972. Typical examples of the protection of reactive functional groups are acylation and etherification for a hydroxy group; acylation, enamination and silylation for an amino group; and esterification, amidation and acid anhydridation for a carboxylic acid.

It should be noted that the term "protection of carboxylic acid" herein used includes the esterification of the carboxylic acid at 3-position for the purpose of obtaining a pharmacologically active ester. The esterification of the compound (Ia) having a free carboxylic acid can be conducted by neutralizing the acid with a base to form a carboxylate, and treating the latter with an acid halide having a proper ester residue.

7. Reaction Conditions

Most of the reactions listed in the above items 1. to 6. are usually carried out at a temperature between −50° and 100° C., particularly, between −20° and 50° C., for 10 minutes to 5 hours in a proper solvent, and if necessary, under anhydrous conditions.

Examples of the solvent employable in the processes of this invention are the following: hydrocarbons (e.g. pentane, hexane, octane, benzene, toluene, xylene), halogenated hydrocarbons (e.g. dichloromethane, chloroform, carbon tetrachloride, dichloroethane, trichloroethane, chlorobenzene), ethers (e.g. diethyl ether, methyl isobutyl ether, dioxane, tetrahydrofuran), ketones (e.g. acetone, methyl ethyl ketone, cyclohexanone), esters (e.g. ethyl acetate, isobutyl acetate, methyl benzoate), nitro hydrocarbons (e.g. nitromethane, nitrobenzene), nitriles (e.g. acetonitrile, benzonitrile), amides (e.g. formamide, acetamide, dimethylformamide, dimethylacetamide, hexamethylphosphorotriamide), sulfoxides (e.g. dimethyl sulfoxide), carboxylic acids (e.g. formic acid, acetic acid, propionic acid), organic bases (e.g. diethylamine, triethylamine, pyridine, picoline, collidine, quinoline), alcohols (e.g. methanol, ethanol, propanol, hexanol, octanol, benzyl alcohol), water, other industrially available solvents and a mixture thereof.

An ultimate product (Ia) of the invention can be isolated from the reaction mixture by any of, or a combination of, the conventional methods such as absorption, elution, distillation, precipitation, concentration, chromatography and the like, after the removal of impurities such as starting materials, by-products and solvents by conventional techniques such as extraction, evaporation, washing, filtration, drying, etc.

Practical and presently preferred embodiments of the invention are illustratively shown in the following Preparations and Examples, wherein physico-chemical data of the products are all listed in Tables I to V; Infra Red (IR) and Nuclear Magnetic Resonance (NMR) data are shown by $\nu(cm^{-1})$ and $\delta(ppm)$ values (coupling constant J in Hz) respectively; part(s) and % are by weight unless otherwise indicated; following abbreviations are employed: Me(=methyl), Et(=Ethyl), Bu(=butyl), Ph(=phenyl), Ac(=acetyl), DMF(=dimethylformamide), PMB(=p-methoxybenzyl), PNB(=p-nitrobenzyl), POM(=pivaloyloxymethyl), Py(pyridine), Het(=heterocyclic group), HP-20(=Diaion HP-20, trade name of styrene divinylbenzene copolymer produced by Mitsubishi Kasei Co., Ltd., Japan), CAN(=ceric ammonium nitrate), m-CPBA(=m-chloroperbenzoic acid), DBU(=1,5-diazabicyclo[5.4.0.]-5-undecene), mM(=millimole),

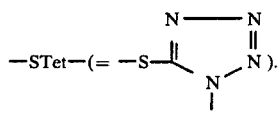

In reviewing the tables, special attention should be paid to the following points: the symbols (a) and (b) set forth in the second column represent respectively R and S configuration of the substituent $R^1$; the symbol α and β in the second column represent respectively α and β configuration of the substituent at the 3-position of the azetidinone ring in Table I and 6-position of the penem ring in the other tables.

Preparation of starting materials

The compound of the invention represented by the formula (Ia) can be prepared by using a carbonylalkylidenephosphorane compound of the formula (II) as a starting material:

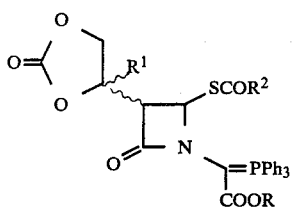

wherein R, $R^1$ and $R^2$ are as defined above.

1. Preparation of starting material (II) wherein $R^2$ is halomethyl

The starting material (II) wherein $R^2$ is a halomethyl group can be prepared according to one of the alternative routes shown below.

1.1. Synthetic route A

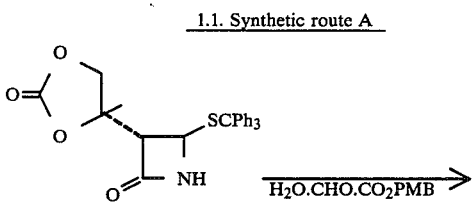

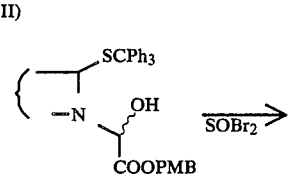

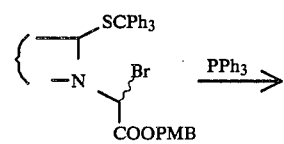

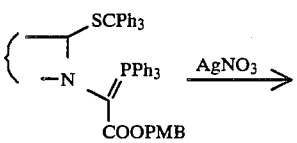

-continued
1.1. Synthetic route A

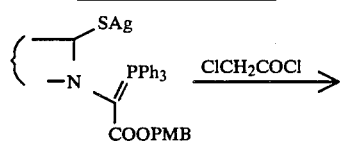

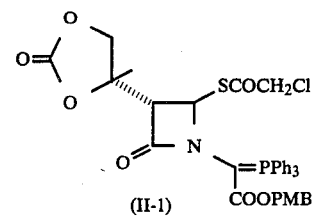

The starting material (III) employed in the above synthetic route A can be obtained according to one of the following synthetic routes A-I to A-IV.

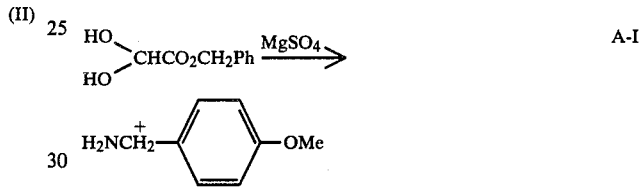  A-I

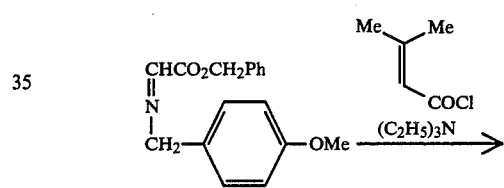

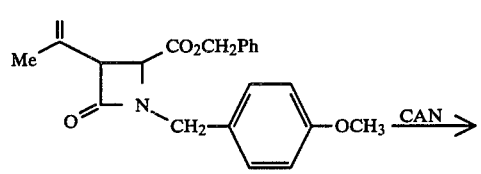

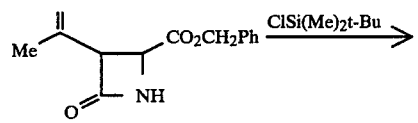

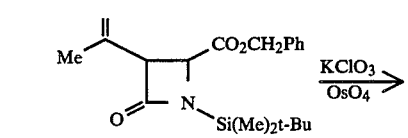

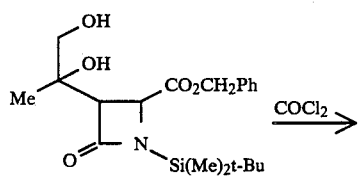

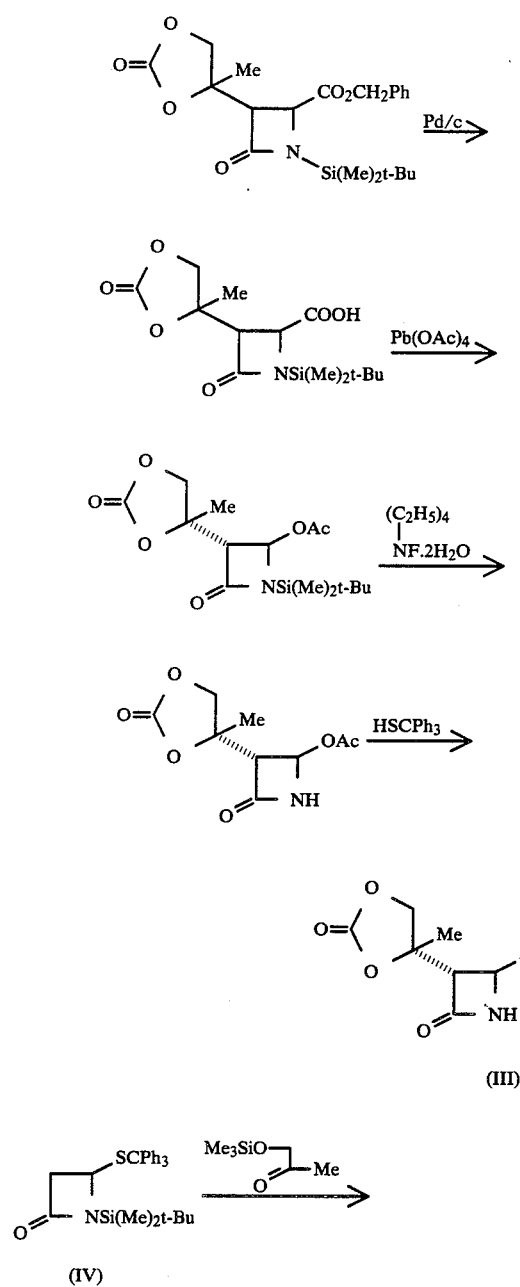
In the above synthetic route, the starting azetidinone derivative (IV) which has the same configuration as penicillin can be prepared according to the following scheme.

11
-continued
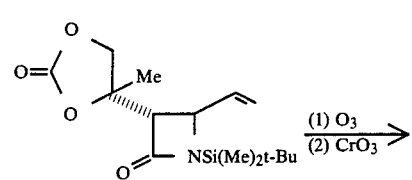
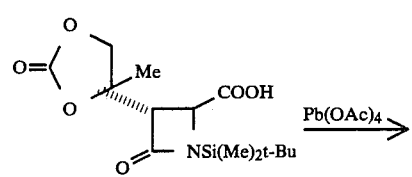
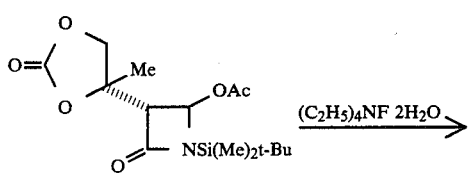
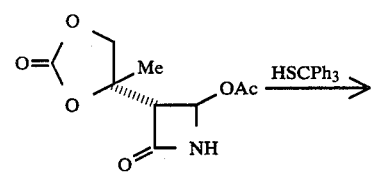
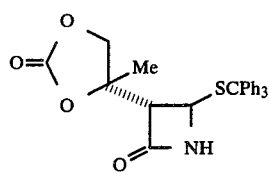
(III)
A-IV
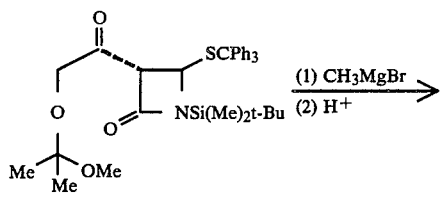
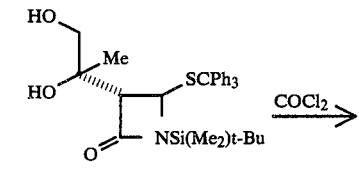
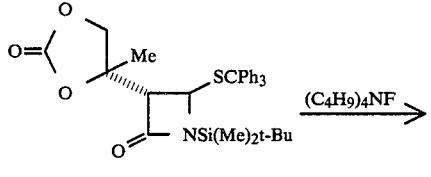
12
-continued
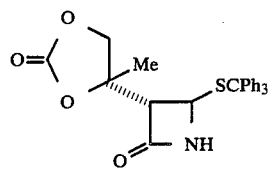
(III)
1.2. Synthetic route B
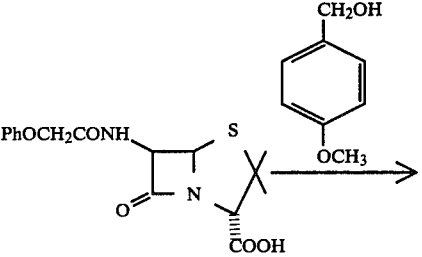
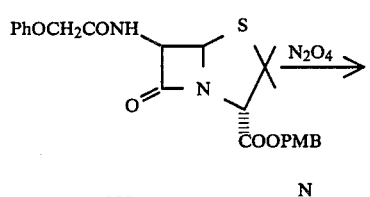
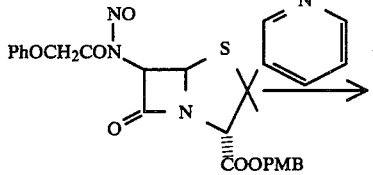
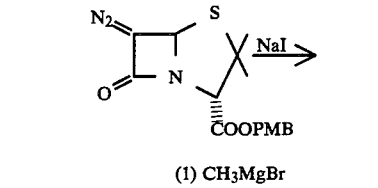
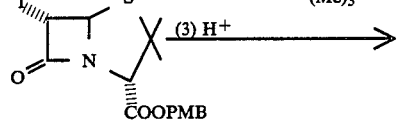
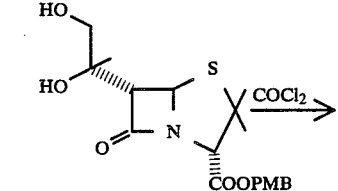
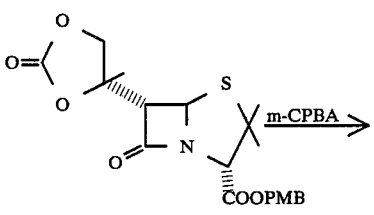

13
-continued
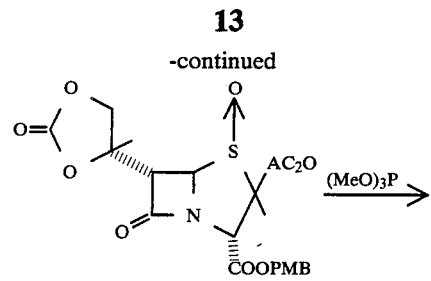
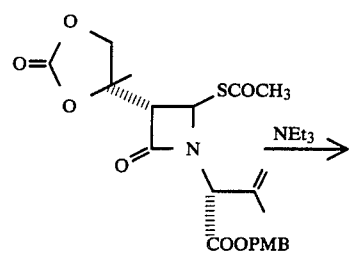
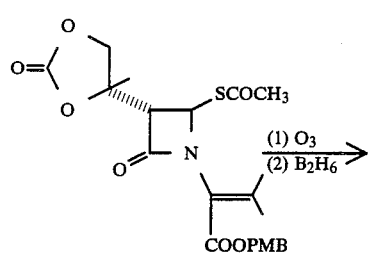
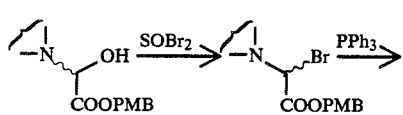
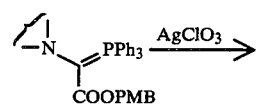
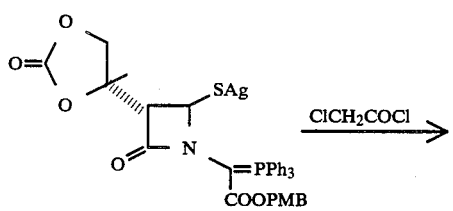
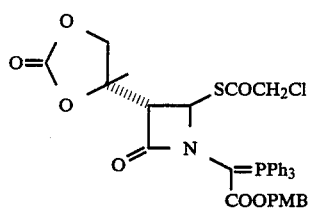
(II)-1
2. Preparation of starting material (II) wherein $R^2$ is methyl
The starting material (II) wherein $R^2$ is methyl can be prepared according to one of the following alternative routes.
2.1. Synthetic route A
14
-continued
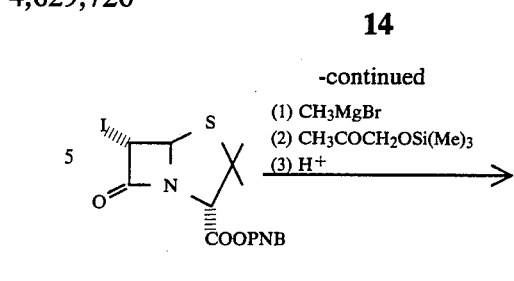
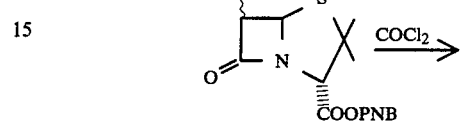
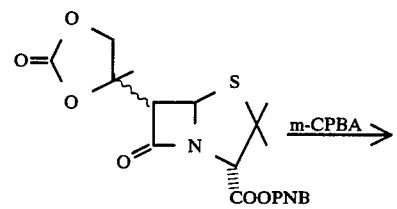
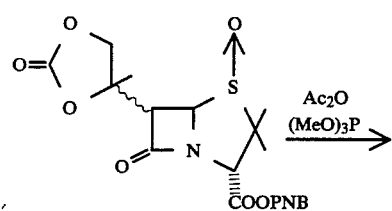
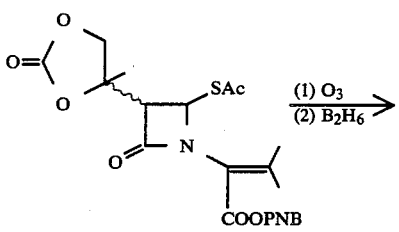
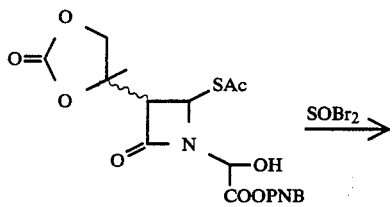
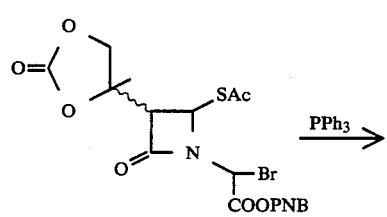

-continued
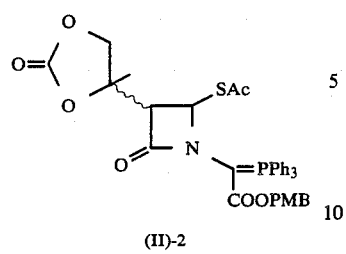
(II)-2
2.2. Synthetic route B
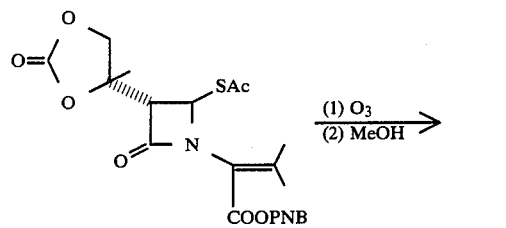
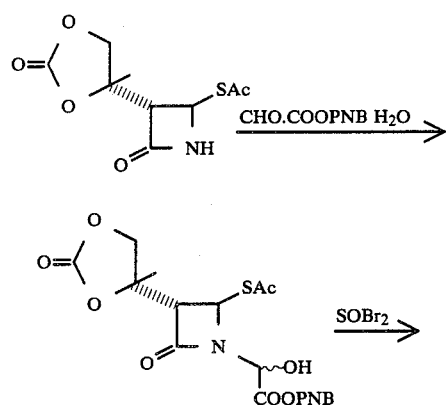
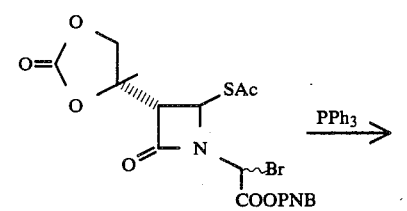
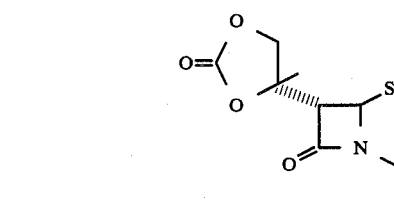
(II)-2
2.3. Synthetic route C
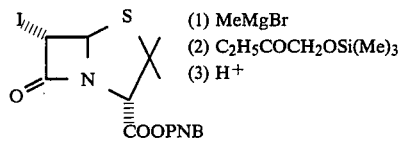
(1) MeMgBr
(2) C₂H₅COCH₂OSi(Me)₃
(3) H⁺
-continued
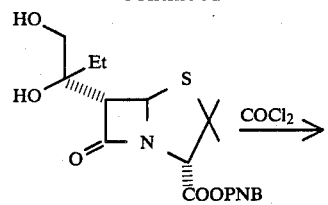
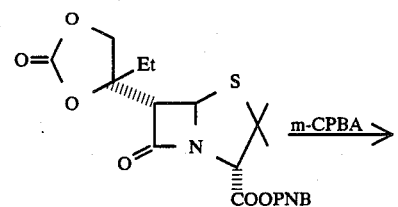
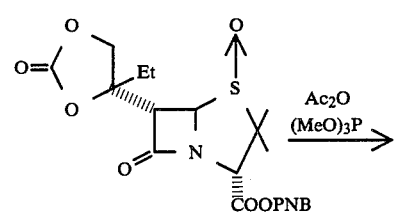
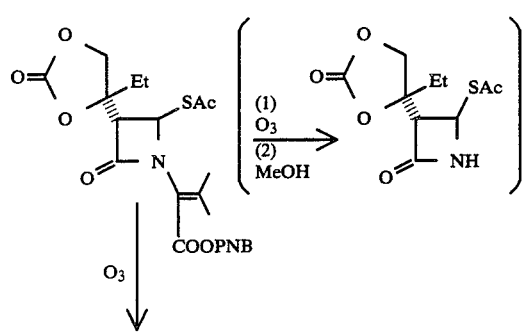
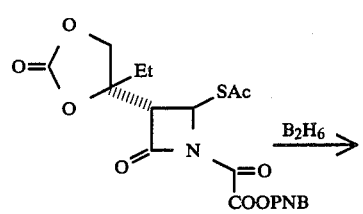
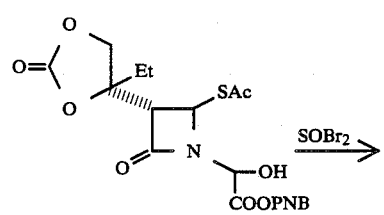
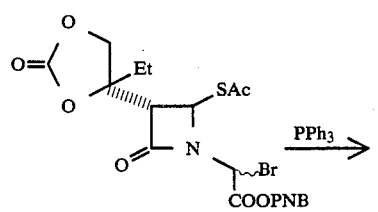

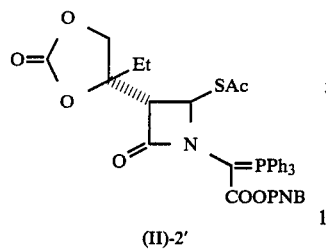
(II)-2'
2.4. Synthetic route D
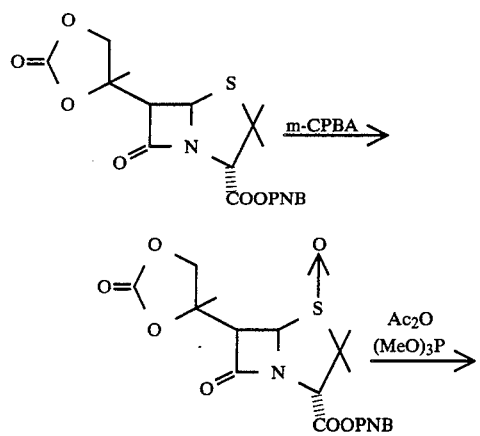
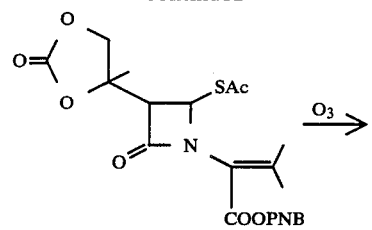
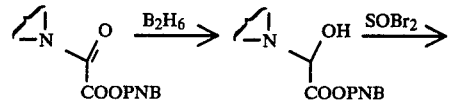
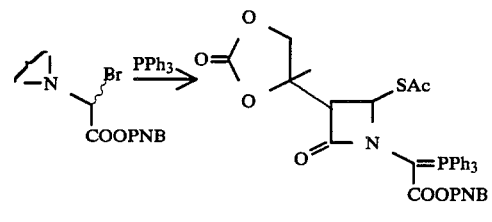
(II)-2
3. Preparation of starting material (II) wherein $R^2$ is hydrogen
The starting material (II) wherein $R^2$ is hydrogen can be prepared according to the following reaction scheme.
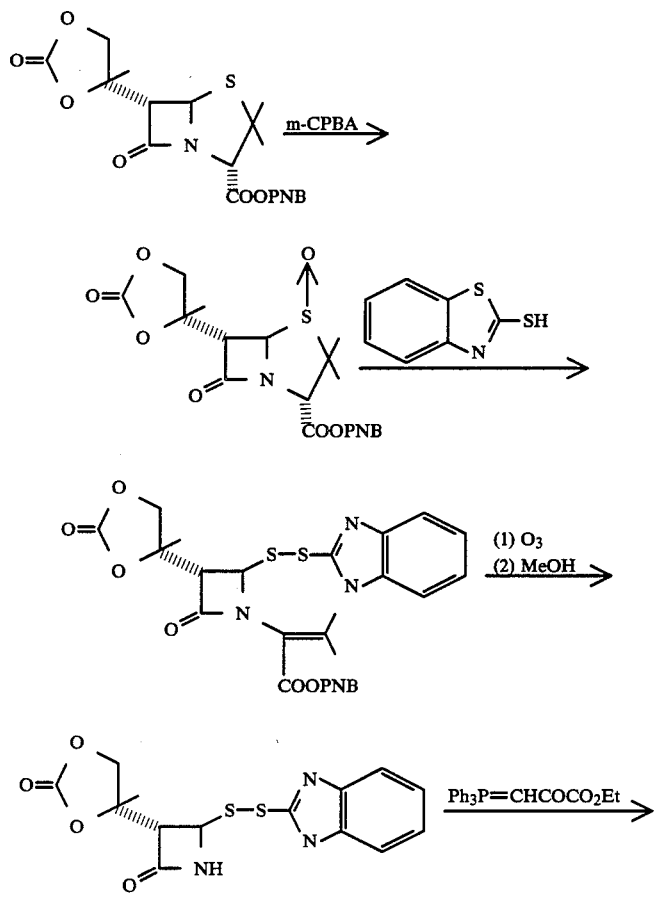

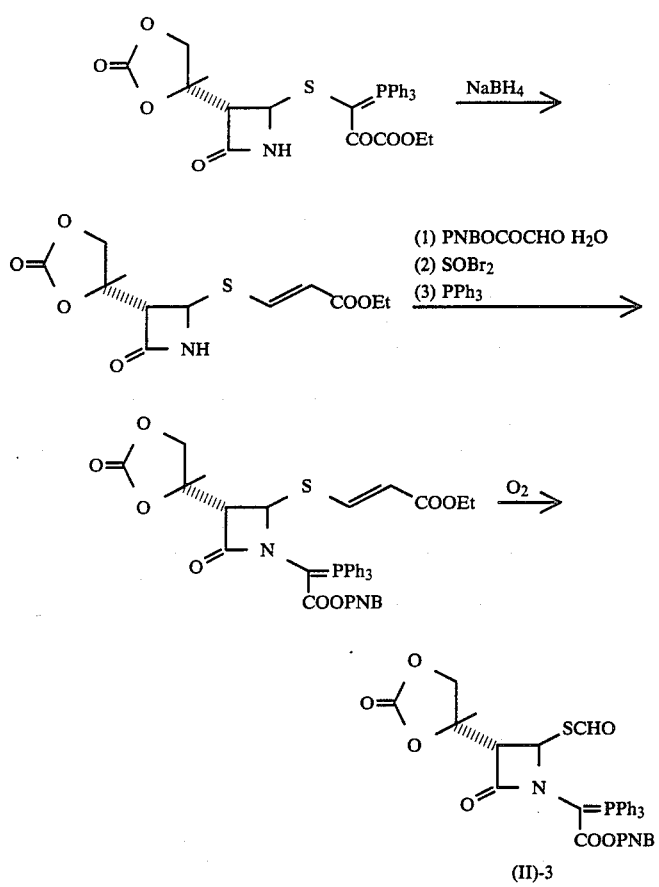
4. Preparation of starting material (II) wherein $R^2$ is acetoxymethyl
The starting material (II) wherein $R^2$ is acetoxymethyl can be prepared according to the synthetic route shown below.
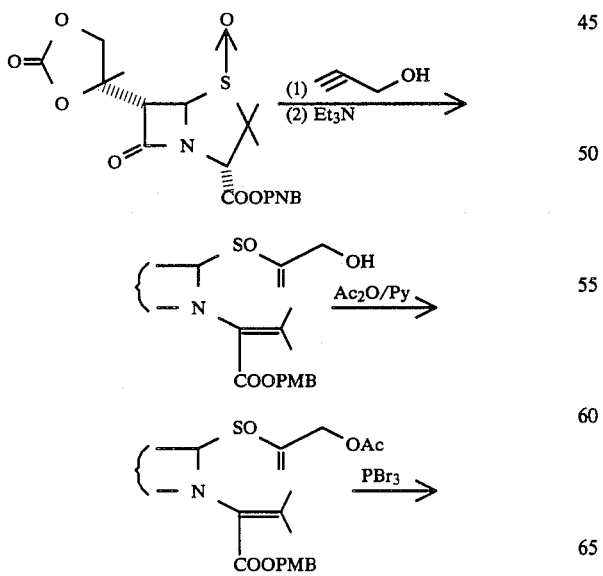
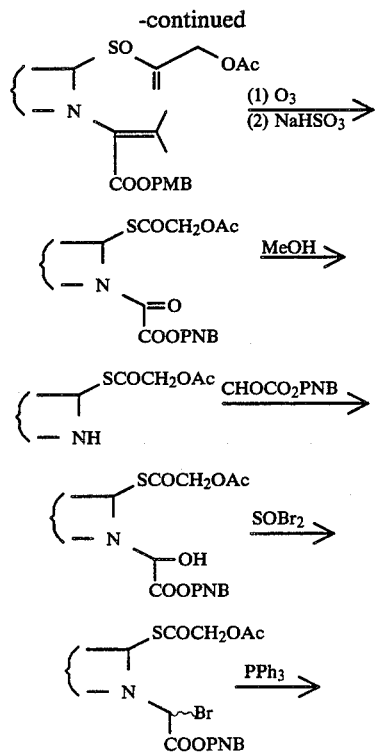

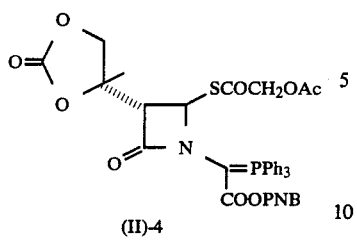

(II)-4

5. Preparation of starting material (II) wherein R² is dimethyl-tert.-butylsilyloxymethyl The starting material (II) wherein R² is dimethyl-tert.-butylsilyloxymethyl(—OSi(Me)₂t—Bu) can be prepared according to the following reaction scheme.

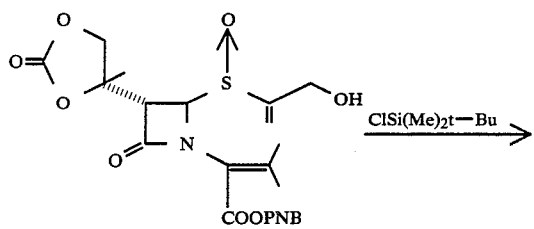

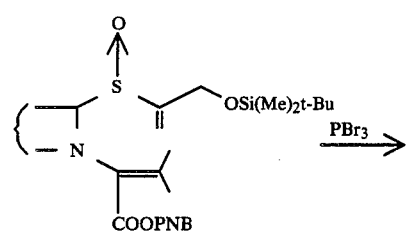

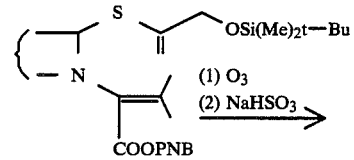

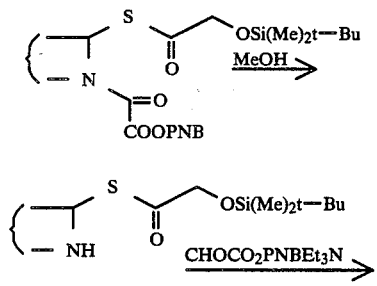

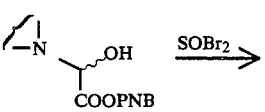

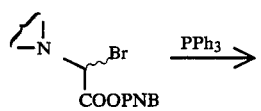

(II)-5

6. Preparation of starting material (II) wherein R² is heterocyclic thiomethyl

The starting compound (II) wherein R² is heterocyclic thiomethyl can be obtained by starting from the aforementioned starting compound (II)-1 in a manner as shown below.

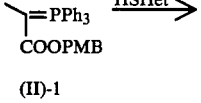

(II)-1

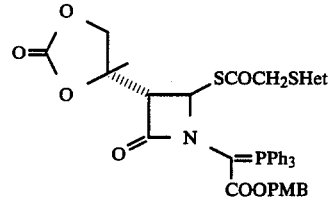

(II)-6

The starting materials (II) obtained by any one of the procedures mentioned above are listed in Table I.

EXAMPLE 1 p-Methoxybenzyl 2-chloromethyl-6-(4-methyl-2-oxo-1,3-dioxolan-4-yl)-2-penem-3-carboxylate (Compound No. 2-1)

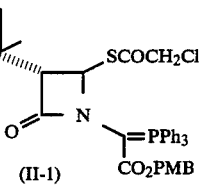

(II-1)

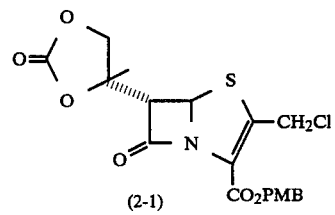

(2-1)

Crude starting compound of the formula (II-1) (1.1 g) dissolved in dry toluene (100 ml) is heated at 85° C. for 2 hours. After completion of the reaction, the solvent is removed under reduced pressure and the residue is purified by chromatography over silica gel using benzene/acetone (4:1) as an eluent. The title compound (2-1) is thus obtained as a foam. Yield: 670 mg.

EXAMPLE 2 p-Methoxybenzyl 2-(1-methyl-5-tetrazolyl)-thiomethyl-6-(4-methyl-2-oxo-1,3-dioxolan-4-yl)-2-penem-3-carboxylate (Compound No. 3-1)

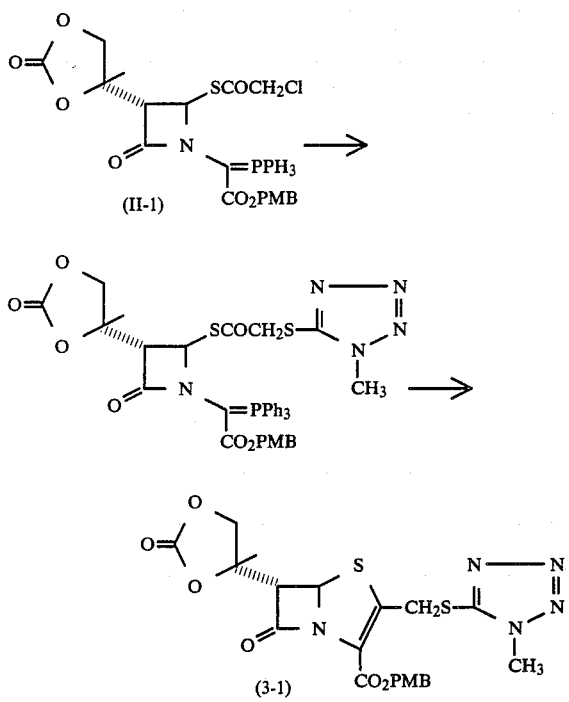

The starting compound (II-1) (248 mg) is dissolved in a mixture of methylene chloride (10 ml) and water (1 ml). To the solution are added sodium salt of 5-mercapto-1-methyl-1,2,3,4-tetrazole (200 mg) and tetra-n-butylammonium bromide (20 mg), and the mixture is stirred at room temperature for 2 hours. The organic phase is separated, washed with saturated aqueous NaHCO₃ solution, and dried over MgSO₄. After evaporation of the solvent, the residue is purified over silica gel using benzene/ethyl acetate (1:3) as an eluent to give the intermediate compound having a tetrazolylthiomethyl group.

Yield: 260 mg.

IR ($\nu_{cm^{-1}}^{CHCl_3}$): 1805, 1755.

The intermediate compound obtained above is dissolved in toluene (20 ml) and the solution is heated at 90° C. for 2 hours. After completion of the reaction, the solvent is vaccum evaporated and the residue is purified by chromatography over silica gel using benzene/ethyl acetate (2:1) to give the desired compound (3-1) as a foam.

Yield: 130 mg.

EXAMPLE 3 p-Methoxybenzyl 2-(1-methyl-5-tetrazolyl)-thiomethyl-6-(4-methyl-2-oxo-1,3-dioxolan-4-yl)-2-penem-3-carboxylate (Compound Nos. 3-1 and 3-4)

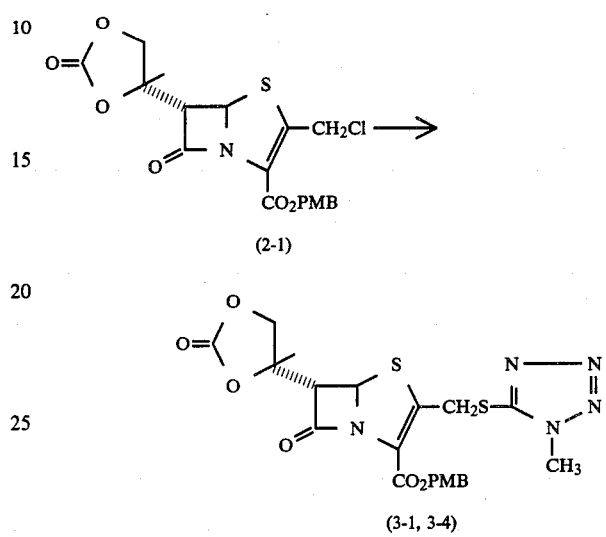

The starting compound (2-1) obtained in Example 1 (40 mg) is dissolved in a mixture of methylene chloride (2 ml) and water (0.5 ml). To the solution are added sodium salt of 5-mercapto-1-methyl-1,2,3,4-tetrazole (19 mg) and tetra-n-butylammonium bromide (3 mg), and the mixture is stirred at room temperature for 2 hours. The organic phase is separated, washed with saturated aqueous NaHCO₃ solution and dried over MgSO₄. The organic solvent is vaccum evaporated and the residue is purified by chromatography over silica gel using benzene/ethyl acetate (2:1) as an eluent. The desired compound (3-1, 3-4) is thus obtained as a foam.

Yield: 38 mg.

In the same manner as in the preceding Examples, various compounds of the formula (Ia) are obtained, which are listed in Tables II and III.

EXAMPLE 4

Sodium 2-(1-methyl-5-tetrazolyl)-thiomethyl-6-(4-methyl-2-oxo-1,3-dioxolan-4-yl)-2-penem-3-carboxylate (Compound Nos. 5-1-5 and 5-1-6)

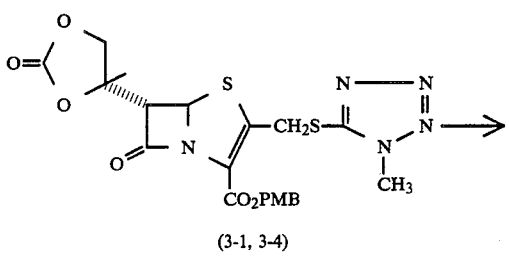

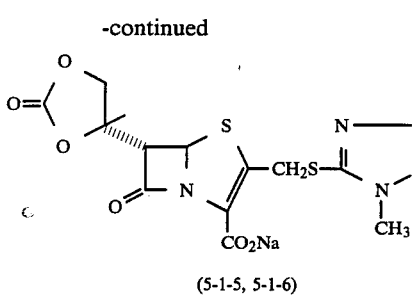

(5-1-5, 5-1-6)

Aluminum chloride (104 mg) is dissolved in a mixture of anisole (2 ml) and methylene chloride (0.2 ml). To the solution is added 100 mg of the starting ester (3-1, 3-4) at −40° C. and the mixture is stirred for one hour at this temperature. A 0.01M phosphate buffer (10 ml) containing $NaHCO_3$ (295 mg) is added to the reaction mixture at −40° C. After addition of methylene chloride (20 ml), the mixture is stirred at 0° C. for 30 minutes, filtered and separated to obtain an aqueous phase. The aqueous phase is purified by HP-20 and lyophilized to give the desired compound as a white powder. Yield: 35 mg.

Various compounds (Ia) obtained in the same manner as in Example 4 are shown in Table IV.

EXAMPLE 5

Pivaloyloxymethyl 2-dimethyl-tert.-butylsilyloxymethyl-6-(4-methyl-2-oxo-1,3-dioxolane-4-yl)-2-penem-3-carboxylate (Compound No. 6-1)

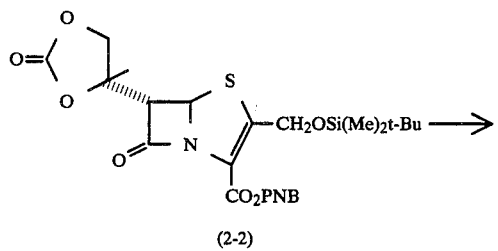

(2-2)

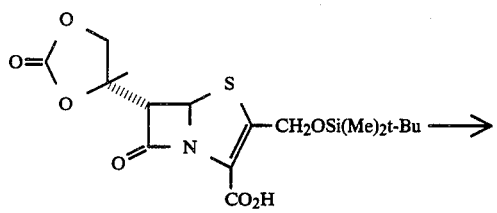

(6-1)

The starting compound (2-2) (120 mg) is dissolved in ethyl acetate (50 ml) and subjected to a catalytic reduction under hydrogen at room temperature in the presence of 10% paradium/carbon (100 mg). Additional paradium/carbon catalysts (100 mg each) are added at one hour interval and the reaction is continued for 6 hours. After completion of the reaction, the solvent is vaccum evaporated to give the intermediate carboxylic acid as a residue. The carboxylic acid is dissolved in DMF (5 ml). To the solution are added triethylamine (40 μl) and pivaloyloxymethyl iodide ($ICH_2OCO_2t$-Bu) (108 μl) and the mixture is stirred for one hour. After completion of the reaction, the mixture is added with ethyl acetate (20 ml) and filtered. The filtrate is washed with water, dried over $MgSO_4$ and vaccum evaporated to remove the solvent. The residue is purified by chromatography over silica gel using benzene/ethyl acetate (2:1) as an eluent to obtain the title compound.

Yield: 70 mg.

Various compounds (Ia) prepared in accordance with the procedure described in Example 5 are summarized in Table V.

TABLE I

| No. | $R^1$ | $R^2$ | R | IR | NMR |
|---|---|---|---|---|---|
| 1-1 | $CH_3$ (a) α | $CH_2Cl$ | PMB | $CHCl_3$: 1805, 1750 | |
| 1-2 | $CH_3$ (a) α | $CH_2S$—(N-methyl-tetrazolyl) | PNB | $CHCl_3$: 1810, 1765 | Rf: 0.14 (benzene/ethyl acetate = 1:2) |
| 1-3 | $CH_3$ (a) α | $CH_3$ | PMB | $CHCl_3$: 1805, 1755 | |
| 1-4 | $CH_3$ (a) α | $CH_3$ | PNB | $CHCl_3$: 1810, 1760, 1705, 1615 | |
| 1-5 | $C_2H_5$ (a) α | $CH_3$ | PNB | $CHCl_3$: 1800, 1755, 1695, 1620 | |
| 1-6 | $CH_3$ (a) α | $CH_2OCOCH_3$ | PNB | $CHCl_3$: 1805, 1745 | |
| 1-7 | $CH_3$ (a) α | $CH_2OSi(Me)_2C_4H_9$ | PNB | $CHCl_3$: 1805, 1750 | |
| 1-8 | $CH_3$ (b) α | $CH_2$—S—(N-methyl-tetrazolyl) | PMB | $CHCl_3$: 1805, 1755 | |

TABLE II

Structure: core bicyclic β-lactam with substituents R¹, R², and COOR group, with dioxolanone attached.

| No. | R¹ | R² | R | IR | NMR |
|---|---|---|---|---|---|
| 2-1 | CH₃ (a) α | CH₂Cl | PMB | CHCl₃: 1815, 1795 | CDCl₃: 1.63(3H,s), 3.80(3H,s), 4.03(1H,d,J=2Hz), 4.20(d) + 4.60(d) (2H,J=9Hz,ABq), 4.64(d) + 4.80(d) (2H,J=8Hz,ABq), 5.20(2H,s), 5.64(1H,d,J=2Hz), 6.87(2H,d,J=8Hz), 7.35 (2H,d,J=8Hz). |
| 2-2 | CH₃ (a) α | CH₂OSi(Me)₂C₄H₉ | PNB | | CDCl₃: 0.12(6H,s), 0.91(9H,s), 1.67(3H,s), 4.07 (1H,d,J=2Hz), 4.27(1H,d,J=9Hz), 4.73(1H,d, J=9Hz), 4.90(2H,s), 5.27(1H,d,J=14Hz), 5.53 (1H,d,J=14Hz), 5.70(1H,d,J=2Hz), 7.67(2H, d,J=9Hz), 8.13(2H,d,J=9Hz). |
| 2-3 | CH₃ (a) α | CH₂OAc | PNB | CHCl₃: 1810, 1800, 1750 | CDCl₃: 1.63(3H,s), 2.07(3H,s), 4.03(1H,d,J=2Hz), 4.23(1H,d,J=9Hz), 4.63(1H,d,J=9Hz), 5.10 (1H,d,J=18Hz), 5.37(2H,s), 5.43(1H,d,J= 18Hz), 5.70(1H,d,J=2Hz), 7.60(2H,d,J=9Hz), 8.23(2H,d,J=9Hz). |
| 2-4 | CH₃ (a) α | H | PNB | Nujol: 1780, 1705 | d₆-DMSO: 1.60(3H,s), 4.37, 4.63(2H,ABq,J=9Hz), 4.68 (1H,d,J=1.5Hz), 5.42(2H,s), 6.02(1H,d,J= 1.5Hz), 7.63(1H,s), 7.87(2H,d,J=9Hz), 8.28(2H,d,J=9Hz). |
| 2-5 | CH₃ (a) β | CH₃ | PNB | CHCl₃: 1800, 1710 | d₆-DMSO: 1.52(3H,s), 2.38(3H,s), 4.38,4.62(2H,ABq, J=9Hz), 4.75(1H,d,J=4Hz), 5.27, 5.55(2H, ABq,J=14Hz), 5.95(1H,d,J=4Hz), 7.73(2H,d, J=9Hz), 8.30(2H,d,J=9Hz). |
| 2-6 | C₂H₅ (a) α | CH₃ | PNB | CHCl₃: 1815, 1790, 1715 | CDCl₃: 0.87-1.23(3H,m), 1.67-2.17(2H,m), 2.37 (3H,s), 4.03-4.2(1H,m), 4.30,4.70(2H,ABq, J=9Hz), 5.17,5.50(2H,ABq,J=13Hz), 5.57-5.75(1H,m), 7.57(2H,d,J=9Hz), 8.18(2H,d,J=9Hz). |
| 2-7 | CH₃ (a) α | CH₂S-[1-methyl-tetrazol-5-yl] | PNB | Nujol: 1810, 1770, 1710 | (insoluble in solvents) |
| 2-8 | CH₃ (a) α | CH₃ | PNB | CHCl₃: 1810, 1790, 1715 | CDCl₃: 1.65(3H,s), 2.37(3H,s), 4.00(1H,d,J=2Hz), 4.22, 4.67(2H,ABq,J=9Hz), 5.18, 5.48(2H, ABq,J=14Hz), 5.62(1H,d,J=2Hz), 7.57(2H,d, J=9Hz), 8.20(2H,d,J=9Hz). |
| 2-9 | CH₃ (b) α | CH₂S-[1-amino-tetrazol-5-yl] | PMB | CHCl₃: 2950, 1810, 1795, 1725 | CDCl₃: 1.59(3H,s), 4.00(1H,d,J=2Hz), 4.03(d) + 4.27(d) (2H,J=7Hz,ABq), 4.50(d) + 4.72(d) (2H,J=8Hz,ABq), 5.20(2H,s), 5.46(2H,s, NH₂), 5.58(1H,d,J=2Hz), 6.85(2H,d,J=8Hz), 7.35(2H,d,J=8Hz). |
| 2-10 | CH₃ (a) α | CH₂S-[1-amino-tetrazol-5-yl] | PMB | CHCl₃: 2950, 1810, 1795, 1725 | CDCl₃: 1.63(3H,s), 3.78(3H,s), 4.09(1H,d,J=2Hz), 4.13(d) + 4.37(d) (2H,J=7Hz,ABq), 4.47(d) + 4.70(d) (2H,J=8Hz,ABq), 5.20(2H,s), 5.51 (1H,d,J=2Hz), 5.87(2H,s,NH₂), 6.85(2H,d, J=8Hz), 7.35(2H,d,J=8Hz). |
| 2-11 | CH₃ (a) α | CH₂S-[1-(2-hydroxyethyl)-tetrazol-5-yl] | PMB | CHCl₃: 3500, 1815, 1795 | CDCl₃: 1.58(3H,s), 3.80(3H,s), 4.00(1H,d,J=2Hz), 4.00-4.40(2H,m), 4.07(2H,t,J=4Hz), 4.35 (2H,t,J=4Hz), 4.44(d) + 4.72(d) (2H,J=8Hz, ABq), 5.18(2H,s), 5.60(1H,d,J=2Hz), 6.85 (2H,d,J=8Hz), 7.35(2H,d,J=8Hz). |

TABLE II-continued

| No. | R¹ | R² | R | IR | NMR |
|---|---|---|---|---|---|
| 2-12 | CH₃ (b) α | N—N, CH₃S—, N, CH₂CONH₂ (triazole) | PMB | CHCl₃: 1810, 1790, 1700 | CDCl₃: 1.63(3H,s), 3.80(3H,s), 4.11(1H,d,J=2Hz), 4.16(d) + 4.43(d) (2H,J=7Hz,ABq), 4.48(d) + 4.72(d) (2H,J=8Hz,ABq), 4.96(2H,s), 5.19 (2H,s), 5.57(1H,d,J=2Hz), 6.85(2H,d,J= 8Hz), 7.35(2H,d,J=8Hz). |
| 2-13 | CH₃ (b) α | N—N, CH₃S—, N, CH₂CH₂OH (triazole) | PMB | CHCl₃: 3500, 1815, 1795 | CDCl₃: 1.63(3H,s), 3.79(3H,s), 4.06(2H,t,J=4Hz), 4.20(1H,d,J=2Hz), 4.00–4.40(m,2H), 4.35 (2H,t,J=4Hz), 4.42(d) + 4.72(d) (2H,J=8Hz, ABq), 5.17(2H,s), 5.59(1H,d,J=2Hz), 6.85 (2H,d,J=8Hz), 7.35(2H,d,J=8Hz). |
| 2-14 | CH₃ (b) α | N—N, CH₃S—, S, H (thiadiazole) | PMB | CHCl₃: 1815, 1795 | CDCl₃: 1.62(3H,s), 3.79(3H,s), 4.08(1H,d,J=2Hz), 4.16(d) + 4.38(d) (2H,J=8Hz,ABq), 4.61(d) + 4.81(d) (2H,J=8Hz,ABq), 5.20(2H,s), 5.59 (1H,d,J=2Hz), 6.89(2H,d,J=8Hz), 7.35(2H, d,J=8Hz), 9.05(1H,s). |
| 2-15 | CH₃ (b) α | N—N, CH₃S—, N, CH₂CH₂OH (triazole) | —CH₂CH=CH₂ | CHCl₃: 3500, 1810, 1790 | CDCl₃: 1.66(3H,s), 3.00(1H,brs,OH), 4.06(2H,t,J= 4Hz), 4.20(1H,d,J=2Hz), 4.00–4.70(6H,m), 4.50(d) + 4.75(d) (2H,J=8Hz,ABq), 5.20– 5.50(2H,m), 5.65(1H,d,J=2Hz), 5.70–6.15 (1H,m). |

TABLE III

| No. | R¹ | R² | R | IR | NMR |
|---|---|---|---|---|---|
| 3-1 | CH₃ (a) α | N—N, CH₃S—, N, CH₃ (triazole) | PMB | CHCl₃: 1815, 1795, UV(EtOH): λmax 328, 227 nm | CDCl₃: 1.56(3H,s), 3.79(3H,s), 3.90(3H,s) 3.99 (1H,d,J=2Hz), 4.15(d) + 4.60(d)(2H,J=9Hz, ABq), 4.54(d) + 4.78(d)(2H,J=8Hz,ABq), 5.18(2H,s), 5.57(1H,d,J=2Hz), 6.85(2H,d, J=8Hz), 7.35(2H,d,J=8Hz). |
| 3-2 | CH₃ (a) α | N—N, CH₃S—, S, H (thiadiazole) | PMB | CHCl₃: 1815, 1795 | CDCl₃: 1.58(3H,s), 3.80(3H,s), 4.00(1H,d,J=2Hz), 4.19(d) + 4.60(d)(2H,J=9Hz,ABq), 4.68(d) + 4.82(d)(2H,J=8Hz,ABq), 5.20(2H,s), 5.60 (1H,d,J=2Hz), 6.89(2H,d,J=8Hz), 7.35(2H, d,J=8Hz), 9.07(1H,s). |
| 3-3 | CH₃ (a) α | N—N, CH₃S—, S, CH₃ (thiadiazole) | PMB | CHCl₃: 1815, 1795 | CDCl₃: 1.59(3H,s), 2.73(3H,s), 3.80(3H,s), 4.00 (1H,d,J=2Hz), 4.17(d) + 4.60(d)(2H,J=9Hz, ABq), 4.62(d) + 4.79(d)(2H,J=8Hz,ABq), 5.20(2H,s), 5.58(1H,d,J=2Hz), 6.87(2H,d, J=8Hz), 7.35(2H,d,J=8Hz). |

TABLE III-continued

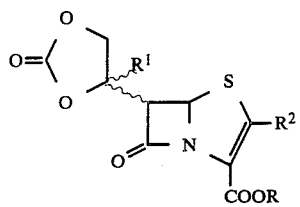

| No. | R¹ | R² | R | IR | NMR |
|---|---|---|---|---|---|
| 3-4 | CH₃ (b) α | N—N, CH₂S—, N-CH₃ (1-methyl-tetrazol-5-yl-thiomethyl) | PMB | CHCl₃: 1815, 1795, | CDCl₃: 1.62(3H,s), 3.79(3H,s), 3.90(3H,s), 4.10 (1H,d,J=2Hz), 4.13(d) + 4.74(d)(2H,J=8Hz, ABq), 4.25(d) + 4.62(d)(2H,J=9Hz,ABq), 5.19(2H,s), 5.59(1H,d,J=2Hz), 6.85(2H,d, J=8Hz), 7.34(2H,d,J=8Hz). |

TABLE IV-1

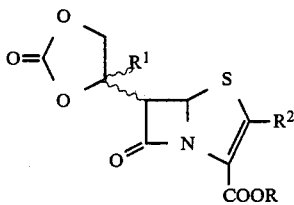

| No. | R¹ | R² | R | IR | NMR |
|---|---|---|---|---|---|
| 5-1-1 | CH₃ (b) α | N—N, CH₂S—, N-NH₂ | Na | UV(H₂O): λmax 312 nm | D₂O: 1.68(3H,s), 4.38(1H,d,J=2Hz), 4.42(d) + 4.58(d)(2H,J=7Hz,ABq), 4.57(2H,s), 5.71 (1H,d,J=2Hz). |
| 5-1-2 | CH₃ (b) α | N—N, CH₂S—, N-CH₂CONH₂ | Na | UV(H₂O): λmax 315 nm | D₂O: 1.68(3H,s), 4.34(1H,d,J=2Hz), 4.40(d) + 4.57(d)(2H,J=7Hz,ABq), 4.49(d) + 4.62(d) (2H,J=8Hz,ABq), 5.36(2H,s), 5.69(1H,d, J=2Hz). |
| 5-1-3 | CH₃ (b) α | N—N, CH₂S—, N-CH₂CH₂OH | Na | UV(H₂O): λmax 310 nm | D₂O: 1.68(3H,s), 4.00(2H,t,J=4Hz), 4.35–4.70 (m,6H), 4.36(1H,d,J=2Hz), 4.38(d) + 4.50 (d)(2H,J=8Hz,ABq), 5.72(1H,d,J=2Hz). |
| 5-1-4 | CH₃ (b) α | N—N, CH₂S—, S-H (thiadiazol) | Na | UV(H₂O): λmax 309 nm | D₂O: 1.67(3H,s), 4.34(1H,d,J=2Hz), 4.38(d) + 4.58(d)(2H,J=7Hz,ABq), 4.59(d) + 4.70(d) (2H,J=8Hz,ABq), 5.68(1H,d,J=2Hz), 9.43 (1H,s). |
| 5-1-5 | CH₃ (a) α | N—N, CH₂S—, N-CH₃ | Na | UV(H₂O): λmax 312 nm | D₂O: 1.62(3H,s), 4.10(3H,s), 4.36(1H,d,J=2Hz), 4.44(d) + 4.65(d)(2H,J=9Hz,ABq), 4.50(d) + 4.74(d)(2H,J=8Hz,ABq), 5.74(1H,d, J=2Hz). |
| 5-1-6 | CH₃ (b) α | N—N, CH₂S—, N-CH₃ | Na | UV(H₂O): λmax 312 nm | D₂O: 1.68(3H,s), 4.09(3H,s), 4.36(1H,d,J=2Hz), 4.41(d) + 4.58(d)(2H,J=8Hz,ABq), 4.44(d) + 4.52(d)(2H,J=8Hz,ABq), 5.70(1H,d, J=2Hz). |
| 5-1-7 | CH₃ (a) α | CH₂Cl | Na | UV(H₂O): λmax | |

TABLE IV-1-continued

| No. | R¹ | R² | R | IR | NMR |
|---|---|---|---|---|---|
| 5-1-8 | $CH_3$ (a) α | $CH_2S-\overset{N---N}{\underset{S}{\parallel}}-CH_3$ | Na | UV($H_2O$): λmax 310 nm | $D_2O$: 1.63(3H,s), 2.74(3H,s), 4.30(1H,d,J=2Hz), 4.42(d) + 4.70(d)(2H,J=7Hz,ABq), 4.50(d) + 4.63(d)(2H,J=8Hz,ABq), 5.70(1H,d, J=2Hz). |
| 5-1-9 | $CH_3$ (a) α | $CH_2S-\overset{N---N}{\underset{S}{\parallel}}-H$ | Na | UV($H_2O$): λmax 309 nm | $D_2O$: 1.62(3H,s), 4.32(1H,d,J=2Hz), 4.41(d) + 4.70(d)(2H,J=7Hz,ABq), 4.58(d) + 4.69(d) (2H,J=8Hz,ABq), 5.70(1H,d,J=2Hz), 9.43 (1H,s). |

TABLE V

| No. | R¹ | R² | R | IR | NMR |
|---|---|---|---|---|---|
| 6-1 | $CH_3$ (a) α | $CH_2OSi(Me)_2C_4H_9$ | POM | $CHCl_3$: 1805, 1975 | $CDCl_3$: 0.11(6H,s), 0.93(9H,s), 1.27(9H,s), 1.67 (3H,s), 4.03(1H,d,J=2Hz), 4.20(1H,d, J=9Hz), 4.60(1H,d,J=9Hz), 4.83(2H,s), 5.57(1H,d,J=2Hz), 5.87(2H,s). |
| 6-2 | $CH_3$ (a) α | $CH_2OAc$ | POM | $CHCl_3$: 1805, 1795 | $CDCl_3$: 1.20(9H,s), 1.63(3H,s), 2.10(3H,s), 4.01 (1H,d,J=2Hz), 4.20(1H,d,J=9Hz), 4.57(1H,d, J=9Hz), 5.20(1H,d,J=18Hz), 5.47(1H,d, J=18Hz), 5.63(1H,d,J=2Hz), 5.80(1H,d, J=6Hz), 5.97(1H,d,J=6Hz). |
| 6-3 | $CH_3$ (a) α | H | POM | $CHCl_3$: 1810, 1795 1740 | $CDCl_3$: 1.22(9H,s), 1.67(3H,s), 4.13(1H,d,J= (1.5Hz), 4.20, 4.63(2H,ABq,J=9Hz), 5.77 (1H,d,J=1.5Hz), 5.78,5.88(2H,ABq,J=6Hz), 7.32(1H,s). |
| 6-4 | $CH_3$ (a) α | $CH_3$ | POM | $CHCl_3$: 1810, 1790, 1740, 1720 | $CDCl_3$: 1.20(9H,s), 1.63(3H,s), 2.35(3H,s), 4.00 (1H,d,J=1.5Hz), 4.18,4.62(2H,ABq,J=9Hz), 5.58(1H,d,J=1.5Hz), 5.80,5.90(2H,ABq, J=6Hz). |
| 6-5 | $CH_2H_5$ (a) α | $CH_3$ | POM | $CHCl_3$: 1810(sh), 1795, 1740(sh), 1720 | $CDCl_3$: 1.05(3H,t,J=7Hz), 1.23(9H,s), 1.85(2H,q J=7Hz), 2.38(3H,s), 4.08(1H,d,J=3Hz), 4.28,4.65(2H,ABq,J=9Hz), 5.67(1H,d, J=3Hz), 5.87,5.97(2H,ABq,J=6Hz). |

What is claimed is:

1. A 2-substituted or unsubstituted-6-(2-oxo-1,3-dioxolan-4-yl)-2-penem-3-carboxylic acid derivative of the formula (Ia):

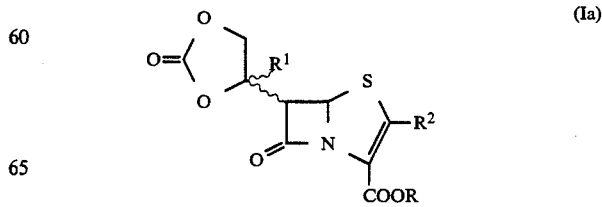

wherein R is hydrogen, sodium, potassium, diphenylmethyl, p-methoxybenzyl, acetoxymethyl, 1-(ethoxycarbonyloxy)ethyl, pivaloyloxymethyl, or p-nitrobenzyl, $R^1$ is methyl, and $R^2$ is hydrogen, methyl, chloromethyl, hydroxymethyl, acetoxymethyl, tri-lower alkoxysilyloxymethyl, thiadiazolylthiomethyl or tetrazolylthiomethyl the last two of said groups being unsubstituted or substituted by methyl, carbamoylmethyl, hydroxyethyl, or amino.

2. A compound as claimed in claim 1 wherein $R^2$ is a substituted methyl group as defined in claim 1.

3. A compound as claimed in claim 1 wherein R is hydrogen, sodium, potassium, diphenylmethyl, p-methoxy-benzyl, acetoxymethyl, 1-(ethoxycarbonyloxy)ethyl or pivaloyloxymethyl.

4. An antibacterial composition which comprises an antibacterially effective amount of a compound according to claim 1 and a pharmaceutically acceptable carrier therefore.

5. A method for combating bacteria which comprises contacting said bacteria with an antibacterially effective amount of a compound according to claim 1.

* * * * *